US012378309B2

(12) United States Patent
Qiu et al.

(10) Patent No.: US 12,378,309 B2
(45) Date of Patent: Aug. 5, 2025

(54) ANTI-HUMAN THYMIC STROMAL LYMPHOPOIETIN (TSLP) MONOCLONAL ANTIBODY AND USE THEREOF TO TREAT DISEASE

(71) Applicant: QYUNS THERAPEUTICS CO., LTD., Jiangsu (CN)

(72) Inventors: Jiwan Qiu, Jiangsu (CN); Yong Kong, Jiangsu (CN); Wei Chen, Jiangsu (CN); Huaiyao Qiao, Jiangsu (CN); Yiliang Wu, Jiangsu (CN); Tao Chen, Jiangsu (CN); Meijuan Wu, Jiangsu (CN)

(73) Assignee: QYUNS THERAPEUTICS CO., LTD., Jiangsu (CN)

( * ) Notice: Subject to any disclaimer, the term of this patent is extended or adjusted under 35 U.S.C. 154(b) by 0 days.

(21) Appl. No.: 18/593,157

(22) Filed: Mar. 1, 2024

(65) Prior Publication Data
US 2024/0352117 A1    Oct. 24, 2024

Related U.S. Application Data

(63) Continuation of application No. PCT/CN2021/136757, filed on Dec. 9, 2021.

(30) Foreign Application Priority Data

Sep. 3, 2021    (CN) .......................... 202111031653.2

(51) Int. Cl.
C07K 16/24    (2006.01)
A61P 37/02    (2006.01)

(52) U.S. Cl.
CPC ............ *C07K 16/244* (2013.01); *A61P 37/02* (2018.01); *C07K 2317/565* (2013.01); *C07K 2317/92* (2013.01)

(58) Field of Classification Search
CPC ............ C07K 16/244; C07K 2317/565; C07K 2317/92; A61P 37/02
See application file for complete search history.

(56) References Cited

U.S. PATENT DOCUMENTS

| 2022/0340654 A1 | 10/2022 | Shi et al. |
| 2022/0363781 A1 | 11/2022 | Xiao et al. |
| 2023/0029835 A1 | 2/2023 | Wang et al. |

FOREIGN PATENT DOCUMENTS

| CN | 101389657 | 3/2009 |
| CN | 101605814 | 12/2009 |
| CN | 106943593 | 7/2017 |
| CN | 107428828 | 12/2017 |
| CN | 109206514 | 1/2019 |
| CN | 109678957 | 4/2019 |
| CN | 110573525 | 12/2019 |
| CN | 111171150 | 5/2020 |
| CN | 111196850 | 5/2020 |
| CN | 112876564 | 6/2021 |
| CN | 113388035 | 9/2021 |
| CN | 113683694 | 11/2021 |
| CN | 114028561 | 2/2022 |
| CN | 114605536 | 6/2022 |
| EP | 1 991 583 | 12/2012 |
| EP | 4 242 229 | 9/2023 |
| WO | 2007/096149 | 8/2007 |
| WO | 2008/076321 | 6/2008 |
| WO | 2016/142426 | 9/2016 |
| WO | 2017/042701 | 3/2017 |
| WO | 2018/191479 | 10/2018 |
| WO | 2020/244544 | 12/2020 |
| WO | 2021/043221 | 3/2021 |
| WO | 2021/155861 | 8/2021 |
| WO | 2022/095689 | 5/2022 |

OTHER PUBLICATIONS

Tahaghoghi-Hajghorbani S, et al. (2019) Autoimmun Highlights. 10:1 (7 pages). (https://doi.org/10.1186/s13317-019-0110-z).*
Nakajima, Saeko et al., "Anti-TSLP antibodies: Targeting a master regulator of type 2 immune response", Allergology International, 2020, No. 69, pp. 197-203.
Liu Xiang et al., "The role of anti-thymic stromal lymphoblastopoietin antibody in biological targeted therapy of bronchial asthma", Journal of Clinical Pulmonology, 2021, vol. 26, Issue 7, pp. 1124-1134, with English abstract.
Li, Xiangqun et al, "Development and characterization of monoclonal antibodies against mouse TSLP", Hybridoma, 2010, vol. 29, No. 5, pp. 425-430.
Zhu, Jian-Guang et al, "Selection and identification of full human scFv against TSLP", Chinese Journal of Immunology, 2014, vol. 12, pp. 1662-1665 and 1669, with English abstract.
Office Action issued Feb. 18, 2022 in Chinese Patent Application No. 202111031653.2, with English-language translation.
Search Report issued Feb. 18, 2022 in Chinese Patent Application No. 202111031653.2, with English-language translation.
International Search Report issued May 13, 2022 in International Application No. PCT/CN2021/136757.
European Office Action issued Feb. 4, 2025, in corresponding European Patent Application No. 21955809.5.

* cited by examiner

*Primary Examiner* — Robert S Landsman
(74) *Attorney, Agent, or Firm* — Wenderoth, Lind & Ponack, L.L.P.

(57) ABSTRACT

Provided in the present invention are an anti-human thymic stromal lymphopoietin (TSLP) monoclonal antibody and the use thereof. The monoclonal antibody has high affinity for human TSLP, has a neutralizing activity, and can be used for preventing or treating TSLP-mediated diseases.

6 Claims, 4 Drawing Sheets
Specification includes a Sequence Listing.

ANTI-HUMAN THYMIC STROMAL LYMPHOPOIETIN (TSLP) MONOCLONAL ANTIBODY AND USE THEREOF TO TREAT DISEASE

CROSS-REFERENCE TO RELATED APPLICATIONS

This application is a continuation application of International Application No. PCT/CN2021/136757, filed Dec. 9, 2021, and claims priority to Chinese Patent Application No. 202111031653.2, filed Sep. 3, 2021, each of which is incorporated by reference herein in its entirety.

REFERENCE TO AN ELECTRONIC SEQUENCE LISTING

The contents of the electronic sequence listing (AttachE_SEQ-0132A.xml; Size: 16,137 bytes; and Date of Creation: Jun. 8, 2024) is herein incorporated by reference in its entirety.

FIELD OF THE INVENTION

The present application relates to the field of antibody drugs. Specifically, the present application relates to a monoclonal antibody against human thymic stromal lymphopoietin (TSLP) and use thereof.

BACKGROUND OF THE INVENTION

Cytokines and immune cells mediate specific physiological mechanisms or pathways, for example, pathways that lead to a variety of inflammatory disorders. Human thymic stromal lymphopoietin (TSLP) is an IL-7-like cytokine produced by human epithelial cells. It promotes B cell differentiation and can also costimulate thymocytes and mature T cells. TSLP binds to specific heterodimeric receptors on human CD11c+ dendritic cells (DCs). This receptor heterodimer consists of a heterodimer of a common gamma-like receptor chain (TSLP receptor; TSLPR) and an IL-7R-α chain. See e.g. Tonozuka et al., Cytogenet. CellGenet. 93:23-25, 2001; Pandey et al., Nat. Immunol. 1:59-64, 2000; L. S. Park et al., J. Exp. Med. 192:659-670, 2000; Reche et al., J. Immunol. 167:336-343, 2001. Ligand binding to the receptor induces DCs to secrete chemical factors that attract TH2, TARC (thymic and activation-regulated chemical factor) and MDC (macrophage-derived chemical factor). In addition, TSLP also induces potent DC activation, expansion of naive $CD^{4+}$ T cells, and subsequent polarization to a TH2 phenotype, producing the pro-allergic cytokines interleukin 4 (IL-4), IL-5, IL-13 and tumor necrosis factor-α.

TSLP signaling was also found to lead to the activation of the STAT5 transcription factor. Moreover, it has been reported that patients with acute and chronic atopic dermatitis overexpress TSLP in skin wounds, indicating that TSLP expression is related to allergic inflammation in vivo. In addition to skin keratinocytes, high levels of TSLP expression have also been found in bronchial epithelial cells, smooth muscle, and lung fibroblasts, supporting a possible role for TSLP in respiratory allergy indications. Furthermore, IgE-activated mast cells express very high levels of TSLP, and this mechanism may be involved in maintaining the TH2 phenotype.

Approximately 20% of the population in Western countries suffers from inflammatory disorders, such as allergic diseases, including asthma, rhinitis, atopic dermatitis and food allergies. 50% to 80% of patients with atopic dermatitis have or develop asthma or allergic rhinitis. To date, there is no cure for allergy-induced asthma, atopic dermatitis, and allergic rhinitis. Current treatments uses, such as beta-2 adrenergic receptor antagonists for asthma, Elidel for atopic dermatitis, and H1-antihistamines for allergic rhinitis, to target these symptoms. There is therefore a growing need in the art for better treatments for these inflammatory disorders, in particular, allergic inflammation. The present application addresses this issue and other issues.

SUMMARY OF THE INVENTION

The purpose of the present application is to provide a new anti-human TSLP monoclonal antibody, a pharmaceutical composition comprising the monoclonal antibody, and a pharmaceutical use thereof.

The technical solutions of the present application are as follows:

1. An anti-human thymic stromal lymphopoietin (TSLP) monoclonal antibody, comprising three heavy chain complementarity determining regions (CDR-H1, CDR-H2 and CDR-H3) and three light chain complementarity determining regions (CDR-L1, CDR-L2 and CDR-L3), wherein:

the amino acid sequence of CDR-H1 (in this specification, CDR-H1 represents heavy chain CDR1) is represented by SEQ ID NO: 1 (SYYMS);

the amino acid sequence of CDR-H2 (in this specification, CDR-H2 represents heavy chain CDR2) is represented by SEQ ID NO: 2 (FISYGGSAYHATWAQG);

the amino acid sequence of CDR-H3 (in this specification, CDR-H3 represents heavy chain CDR3) is represented by SEQ ID NO: 3 (EFRSMTYGAEWGI);

the amino acid sequence of CDR-L1 (in this specification, CDR-L1 represents light chain CDR1) is represented by SEQ ID NO: 4 (QASESIYDTLA);

the amino acid sequence of CDR-L2 (in this specification, CDR-L2 represents light chain CDR2) is represented by SEQ ID NO: 5 (SASSLAS); and the amino acid sequence of CDR-L3 (in this specification, CDR-L3 represents light chain CDR3) is represented by SEQ ID NO: 6 (QQGYTMPDVDKNP).

2. The monoclonal antibody according to item 1, which comprises a heavy chain variable region and a light chain variable region, wherein the amino acid sequence of the heavy chain variable region is represented by SEQ ID NO: 7, its amino acid sequence is

EVQLVESGGGLVQPGGSLRLSCAASGFSLSSYYMSWVRQAPGKGLEWVGF

ISYGGSAYHATWAQGRFTISKDNSKNTLYLQMNSLRAEDTAVYYCAREFR

SMTYGAEWGIWGQGTLVTVSS;

and the amino acid sequence of the light chain variable region is represented by SEQ ID NO: 8, its amino acid sequence is

AYQMTQSPSSVSASVGDRVTITCQASESIYDTLAWYQQKPGKAPKLLIYS

ASSLASGVPSRFSGSGSGTDFTLTISSLQPEDFATYYCQQGYTMPDVDKN

PFGGGTKVEIK.

3. An isolated nucleic acid encoding the monoclonal antibody according to any of the preceding items.

4. A host cell comprising the nucleic acid according to item 3.

The nucleic acid can exist on a vector. The vector can belong to any type, e.g., a recombinant carrier, such as an expression carrier. Any of a variety of host cells can be used. In one embodiment, the host cell is a prokaryotic cell, such as E. coli. In another embodiment, the host cell is a eukaryotic cell, e.g. a mammalian cell, such as a Chinese Hamster Ovary (CHO) cell.

5. A method for producing a monoclonal antibody, which comprises culturing the host cell according to item 4 to produce the monoclonal antibody according to any of the preceding items.

The method comprises expressing a recombinant vector encoding the anti-human TSLP monoclonal antibody in a suitable host cell, thereby producing the monoclonal antibody. In certain embodiments, the method comprises culturing a host cell comprising nucleic acids encoding the anti-human TSLP monoclonal antibody to express the nucleic acids. The method can further comprise recovering the anti-human TSLP monoclonal antibody from a host cell culture or host cell culture medium.

6. A pharmaceutical composition, which comprises the monoclonal antibody according to any of the preceding items and a pharmaceutically acceptable carrier.

The pharmaceutical composition can further comprise an additional therapeutic agent (such as different anti-human TSLP antibodies).

7. The pharmaceutical composition according to item 6, which is used for treating a disease related to TSLP-mediated signal transduction.

8. The pharmaceutical composition according to item 7, wherein the disease related to TSLP-mediated signal transduction is selected from the group consisting of: allergic asthma, allergic dermatitis, allergic rhinitis, allergic conjunctivitis, atopic dermatitis, fibrosis, and inflammatory bowel disease.

9. Use of the monoclonal antibody according to any of the preceding items in the preparation of a medicament for treatment of a disease related to TSLP-mediated signal transduction.

10. The use according to item 9, wherein the disease related to TSLP-mediated signal transduction is selected from the group consisting of: allergic asthma, allergic dermatitis, allergic rhinitis, allergic conjunctivitis, atopic dermatitis, fibrosis, and inflammatory bowel disease.

11. A method for treating a disease related to TSLP-mediated signal transduction, which comprises:
administering the monoclonal antibody or pharmaceutical composition according to any of the preceding items to a subject in need thereof.

12. The method according to item 11, wherein the disease related to TSLP-mediated signal transduction is selected from the group consisting of: allergic asthma, allergic dermatitis, allergic rhinitis, allergic conjunctivitis, atopic dermatitis, fibrosis, and inflammatory bowel disease.

The present application provides a new anti-human TSLP monoclonal antibody, which has comparable affinity for binding to TSLP compared with existing anti-human TSLP monoclonal antibodies (Tezepelumab is a monoclonal antibody drug targeting TSLP developed by Amgen/AstraZeneca, and Tezepelumab has been successfully used in the third phase clinical NAVIGATOR treatment of severe asthma), and its neutralizing activity at the cellular level is superior to Tezepelumab.

The monoclonal antibody of the present application exhibits superior neutralizing activity comparable to Tezepelumab (expressed and prepared according to the sequences disclosed in a patent) at the cellular level, and it is expected to show good clinical effects in the prevention and treatment of related diseases.

BRIEF DESCRIPTION OF THE DRAWINGS

The accompanying drawings are used for a better understanding of the present application and do not constitute an undue limitation of the present application.

wherein.

DETAIL DESCRIPTION OF THE INVENTION

Figure 1:
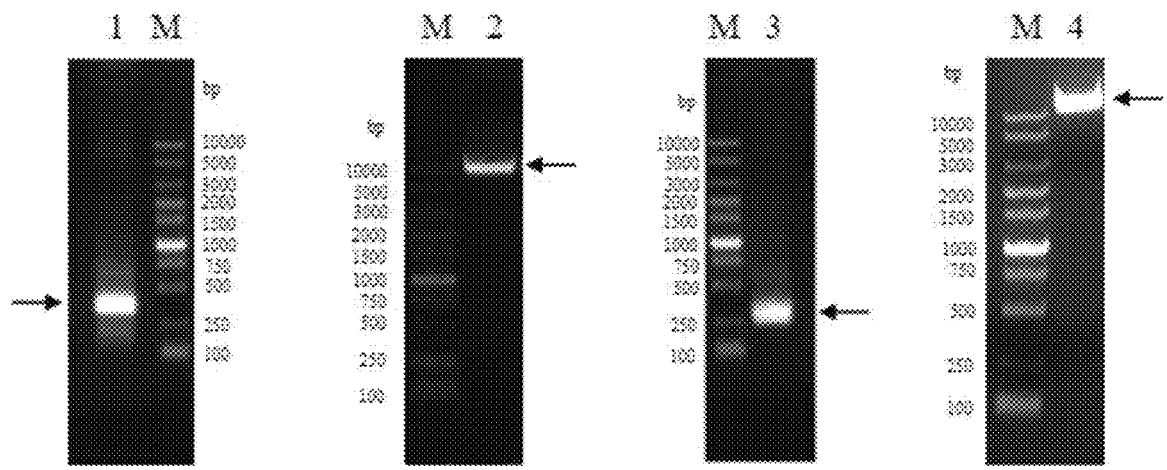
FIG. 1 shows the results of nucleic acid electrophoresis of the constructed HZD8G2-57 transient expression plasmid, wherein M: Marker; Band 1: PCR product 8G2VH-Hu27; Band 2: pHZDCH, HindIII/NheI; Band 3: PCR product 8G2VK-Hu14; Band 4: pHZDCK, HindIII/BsiWI.

Exemplary embodiments of the present application are described below, including various details of the embodiments of the present application to facilitate understanding, and they should be considered to be exemplary only. Accordingly, those of ordinary skill in the art will recognize that various changes and modifications can be made to the embodiments described herein without departing from the scope and spirit of the present application. Also, descriptions of well-known functions and constructions are omitted from the following description for clarity and conciseness.

The scientific and technical terms mentioned in this specification have the same meanings as those commonly understood by those skilled in the art. If there is any conflict, the definitions in this specification shall prevail.

Generally, the terms used in this specification have the following meanings.

In this specification, an "isolated" antibody is an antibody that has been separated from components of its natural environment. In certain embodiments, the antibody is purified to a purity greater than 95% or 99%, which is determined by, for example, electrophoresis (e.g., SDS-PAGE isoelectric focusing (IEF), capillary electrophoresis) or chromatography (e.g., ion exchange or reverse-phase HPLC). For a review of methods for assessing antibody purity, see, for example, Flatman et al., J. Chromatogr. B848: 79-87 (2007).

In this specification, "monoclonal antibody" means an antibody derived from a population of substantially homologous antibodies, i.e., individual antibodies constituting the population are identical and/or bind the same epitope, except for possible variant antibodies (for example, comprising naturally occurring mutations or arising during the production process of monoclonal antibody products), such variants are usually present in trace amounts. Unlike polyclonal antibody products that typically comprise different antibodies directed against different determinants (epitopes), each monoclonal antibody of the monoclonal antibody products is directed against a single determinant on the antigen. Thus, the modifier "monoclonal" indicates the characteristics that the antibody is derived from a substantially homogeneous population of antibodies and should not be construed as requiring production of the antibody by any particular method. For example, the monoclonal antibody to be used according to the present application can be prepared by a variety of techniques, including, but not limited to, a hybridoma method, a recombinant DNA method, a phage display method, and a method using transgenic animals comprising all or part of the human immunoglobulin locus, such methods and other exemplary methods for preparing monoclonal antibodies are described herein.

In this specification, "affinity" means the strength of the sum of the non-covalent interactions between a single binding site of a molecule (e.g., an antibody) and its binding partner (e.g., an antigen). Unless otherwise indicated, "binding affinity" as used in this specification means an intrinsic binding affinity that reflects a 1:1 interaction between members of a binding pair (e.g., antibody and antigen). The affinity of a molecule X for its partner Y can usually be denoted by the equilibrium dissociation constant ($K_D$). Affinity can be measured by common methods known in the art.

In this specification, Human Thymic Stromal Lymphopoietin (TSLP) means a cytokine derived from humans, and its amino acid sequence is represented by SEQ ID NO: 9, wherein the underlined part represents the signal peptide.

SEQ ID NO: 9:
MFPFALLYVLSVSFRKIFILQLVGLVLTYDFTNCDFEKIKAAYLSTISKD

LITYMSGTKSTEFNNTVSCSNRPHCLTEIQSLTFNPTAGCASLAKEMFAM

KTKAALAIWCPGYSETQINATQAMKKRRKRKVTTNKCLEQVSQLQGLWRR

FNRPLLKQQ

In this specification, "anti-human TSLP monoclonal antibody" means a monoclonal antibody that is capable of binding human TSLP with sufficient affinity such that the monoclonal antibody can be used as a diagnostic agent and/or therapy agent targeting human TSLP.

The anti-human TSLP monoclonal antibody of the present application does not bind to a target irrelevant protein. Herein, "irrelevant protein" refer to proteins other than the target human TSLP; herein, "not bind to . . . " refers to in case of the binding ability of the anti-human TSLP monoclonal antibody in the present application to the human TSLP as its target is taken as 100%, the binding ability of the anti-human TSLP monoclonal antibody of the present application to the irrelevant protein is less than 10%, e.g. 9%, 8%, 7%, 6%, 5%, 4%, 3%, 2%, 1% or 0.

The anti-human TSLP monoclonal antibody of the present application may not bind to TSLP of other animal species. Herein, "other animal species" refers to other animal species other than humans, e.g. marmosets, cynomolgus monkeys, pigs, dogs, rabbits, rats, mice, guinea pigs, etc.; herein, "not bind to" refers to: in case of the binding ability of the anti-human TSLP monoclonal antibody of the present application to the human TSLP as its target is taken as 100%, the binding ability of the anti-human TSLP monoclonal antibody of the present application to TSLP of other animal species is less than 10%, e.g. 9%, 8%, 7%, 6%, 5%, 4%, 3%, 2%, 1% or 0.

The human TSLP monoclonal antibody of the present application has an equilibrium dissociation constant ($K_D$) of ≤1 µM, ≤100 nM, ≤50 nM, or ≤40 nM.

Experimental results show that the anti-human TSLP monoclonal antibody of the present application can specifically bind to human TSLP.

The anti-human TSLP monoclonal antibody of the present application is comparable to or superior to similar monoclonal antibody products on the market in terms of many biological activities. The biological activities include, for example, the activities of neutralizing STAT5 phosphorylation in cells induced by human, natural, and cynomolgus monkey TSLP, the activities of neutralizing the release of TARC (CCL17) from human whole blood and human PBMC cells induced by human TSLP, etc.

In a specific embodiment, the amino acid sequence of the heavy chain of the anti-human TSLP monoclonal antibody of the present application is represented by SEQ ID NO: 10; and the amino acid sequence of the light chain of the anti-human TSLP monoclonal antibody of the present application is represented by SEQ ID NO: 11.

SEQ ID NO: 10
EVQLVESGGGLVQPGGSLRLSCAASGFSLSSYYMSWVRQAPGKGLEWVGF

ISYGGSAYHATWAQGRFTISKDNSKNTLYLQMNSLRAEDTAVYYCAREFR

SMTYGAEWGIWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K

SEQ ID NO: 11
AYQMTQSPSSVSASVGDRVTITCQASESIYDTLAWYQQKPGKAPKLLIYS

ASSLASGVPSRFSGSGSGTDFTLTISSLQPEDFATYYCQQGYTMPDVDKN

PFGGGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

Particularly, SEQ ID NO: 10 and 11 are both humanized sequences.

In this specification, "isolated" nucleic acid means a nucleic acid molecule that has been separated from a component of its natural environment. An isolated nucleic acids comprises a nucleic acid molecule typically found in cells comprising a nucleic acid molecule, but the nucleic acid molecule is present extrachromosomally or in a chromosome position different from its natural chromosomal position.

In this specification, "isolated nucleic acid encoding an anti-TSLP monoclonal antibody" means one or more nucleic acid molecules encoding the heavy and light chains of the antibody, including such nucleic acid molecules in a single carrier or separate carriers, and such nucleic acid molecules present in one or more positions in host cell.

In this specification, "carrier" means a nucleic acid molecule capable of amplifying another nucleic acid to which it is linked. The term includes a vector that is a self-replicating nucleic acid structure as well as a vector that integrates into the genome of a host cell into which it has been introduced. Certain vectors are capable of guiding the expression of a nucleic acid to which they are operably linked. Such vectors are referred to herein as "expression vectors."

In this specification, "host cell", "host cell line" and "host cell culture" are used interchangeably and refer to a cell into which exogenous nucleic acid has been introduced, including progeny of such a cell. Host cells include "transformants" and "transformed cells," which include primary transformed cells and progeny derived therefrom (regardless of passage number). The progeny may not be identical in nucleic acid content to the parent cell, but may contain mutations. Mutant progeny that have the same function or biological activity screened or selected from the originally transformed cells are included in this specification.

In this specification, "pharmaceutical composition" means a product that presents a form in which the biological activity of the active ingredients contained therein can be effectively exerted, and the composition does not comprise any additional components with unacceptable toxicity to the subjects to be administered with the formulation.

In this specification, "pharmaceutically acceptable carrier" means an ingredient in a pharmaceutical composition other than an active ingredient that is nontoxic to a subject. Pharmaceutically acceptable carriers include, but are not limited to, buffers, excipients, stabilizers or preservatives.

In the present application, "monoclonal antibodies" are generally human antibodies, which can be prepared using techniques well known to those skilled in the art. For example, human antibodies are generally described in van Dijk, M. A. and vande Winkel, J. G., Curr. Opin. Pharmacol. 5:368-374 (2001) and Lonberg, N., Curr. Opin. Immunol. 20:450-459 (2008).

Antibodies can be prepared by administering immunogens to transgenic animals that have been modified to produce intact human antibodies or intact antibodies with human variable regions when stimulated by antigen challenge. These animals typically comprise part or all of the human immunoglobulin locus, which replace the endogenous immunoglobulin locus or present extrachromosomally or randomly integrated in the animal. In such transgenic mice, the endogenous immunoglobulin loci have generally been inactivated. For a review of methods for obtaining human antibodies from transgenic animals, see Lonberg, N., Nat. Biotech. (Nature Biotechnology) 23:1117-1125 (2005), also see, for example, the XENOMOUSE™ technology described in U.S. Pat. Nos. 6,075,181 and 6,150,584; the HUMAB® technology described in U.S. Pat. No. 5,770,429; the K-MMOUSE® technology described in U.S. Pat. No. 7,041,870, and the VELOCIMOUSE® technology described in U.S. Patent Application Publication No. US 2007/0061900. Human variable regions of intact antibodies generated from such animals can be further modified, for example, by combining with different human constant regions.

Human antibodies can also be prepared by hybridoma-based methods. Human myeloma and mouse-human hybrid myeloma cells have been described for the production of human monoclonal antibodies (see, e.g., Kozbor, D., J. Immunol. 133:3001-3005 (1984); Brodeur, B. R. et al., Monoclonal Antibody Production Techniques and Applications, Marcel Dekker, Inc., New York (1987), pp. 51-63; Boerner, P. et al., J. Immunol. 147:86-95 (1991)). Human antibodies produced via human B-cell hybridoma technology are also described in Li, J. et al., Proc. Natl. Acad. Sci. USA 103:3557-3562 (2006). Other methods include those described, for example, in U.S. Pat. No. 7,189,826 (which describes the generation of monoclonal human IgM antibodies from hybridoma cell lines) and Ni, Xiandai Mianyixue, 26 (4); 265-268 (which describes human-human hybridoma). Human hybridoma technology (Trioma technology) is also described in Vollmers, H. P. and Brandlein, S., Histology and Histopathology 20:927-937 (2005); Vollmers, H. P. and Brandlein, S., Methods and Findings in Experimental and Clinical Pharmacology 27:185-191 (2005).

Human antibodies can also be produced by isolating Fv clone variable domain sequences selected from human-derived phage display libraries, and such variable domain sequences can then be combined with desired human constant domains.

Human antibodies can also be isolated based on the selection of human antibodies from antibody libraries, i.e., by screening for antibodies with one or more activities from the combinatorial libraries. For example, various methods for producing phage display libraries and screening for antibodies with desired binding characteristics from such libraries are known in the art. This approach is reviewed, for example, in Hoogenboom, H. R. et al., Methods in Molecular Biology 178:1-37 (2001), and further described, for example, in McCafferty, J. et al., Nature 348:552-554 (1990); Clackson, T. et al., Nature 352:624-628 (1991); Marks, J. D. et al., J. Mol. Biol. 222:581-597 (1992); Marks, J. D. and Bradbury, A., Methods in Molecular Biology 248:161-175 (2003); Sidhu, S. S. et al., J. Mol. Biol. 338:299-310 (2004); Lee, C. V. et al., J. Mol. Biol. 340:1073-1093 (2004); Fellouse, F. A., Proc. Natl. Acad. Sci. USA 101:12467-12472 (2004); and Lee, C. V. et al., J. Immunol. Methods 284:119-132 (2004).

In certain phage display methods, repertoires of VH and VL genes are cloned separately by polymerase chain reaction (PCR) and recombined randomly in a phage library, which is then screened for antigen-binding phage in the phage library, as described in Winter, G. et al., Ann. Rev. Immunol. 12:433-455 (1994). Phage typically display antibody fragments as single-chain Fv (scFv) fragments or as Fab fragments. Libraries from immunized sources provide high affinity antibodies to the immunogen without the requirement of constructing hybridomas. Alternatively, the naive repertoire can be cloned (e.g., from a human) to provide a single source of antibodies against a wide range of non-self and also self antigens without any immunization, as described in Griffiths, A. D. et al., EMBO J, 12:725-734 (1993). Finally, naive libraries can also be generated synthetically by cloning unrearranged V gene segments from stem cells and rearranging in vitro using PCR primers containing random sequences to encode the highly variable CDR3 region, as described in Hoogenboom, H. R. and Winter, G., J. Mol. Biol. 227:381-388 (1992). Patent publications describing human antibody phage libraries include, for example: U.S. Pat. No. 5,750,373, and U.S. Patent Publication Nos. 2005/0079574, 2005/0119455, 2005/0266000, 2007/0117126, 2007/0160598, 2007/0237764, 2007/0292936 and 2009/0002360.

The antibody may also be a multispecific antibody, such as a bispecific antibody. Bispecific antibodies are monoclonal antibodies that have binding specificities for at least two different sites. Techniques for making multispecific antibodies include, but are not limited to, recombinant co-expression of two immunoglobulin heavy chain-light chain pairs with different specificities (see Milstein, C. and Cuello, A. C., Nature 305:537-540 (1983); WO 93/08829; and Traunecker, A. et al., EMBO J. 10:3655-3659 (1991)) and "knob-in-hole" engineering (see, e.g., U.S. Pat. No. 5,731,168). It is also possible to generate multispecific antibodies by the following methods: engineering electrostatic manipulation effect for making Fc heterodimer molecules of antibodies (WO 2009/089004); cross linking two or more antibodies or fragments (see e.g. U.S. Pat. No. 4,676,980 and Brennan, M. et al., Science 229:81-83 (1985)); using leucine zippers to make bispecific antibodies (see e.g. Kostelny, S. A. et al., J. Immunol. 148:1547-1553 (1992)); using "diabody" technology for making bispecific antibody fragments (see, e.g., Holliger, P. et al., Proc. Natl. Acad. Sci. USA 90:6444-6448 (1993)); using single chain Fv (scFv) dimers (see, e.g., Gruber, M. et al., J. Immunol. 152:5368-5374 (1994)); and preparing trispecific antibodies (e.g., Tutt, A. et al, J. Immunol. 147:60-69 (1991)).

The monoclonal antibodies described herein also include engineered antibodies having three or more functional antigen binding sites, including "octopus antibodies" (see e.g. US 2006/0025576).

Antibodies herein may also include multispecific antibodies disclosed in WO 2009/080251, WO 2009/080252, WO 2009/080253, WO 2009/080254, WO 2010/112193, WO 2010/115589, WO2010/136172, WO 2010/145792, and WO 2010/145793, WO 2011/117330, WO 2012/025525, WO 2012/025530, WO 2013/026835, WO 2013/026831, WO 2013/164325, or WO 2013/174873.

The monoclonal antibodies described herein may also be antibody variants, e.g., it may be desirable to improve the binding affinity and/or other biological properties of the antibody. Amino acid sequence variants of antibodies can be prepared by introducing appropriate modifications into the nucleotide sequence encoding the antibody, or by peptide synthesis. Such modifications include, for example, deletions, and/or insertions and/or substitutions of residues within the amino acid sequence of the antibody. Any combination of deletions, insertions, and substitutions can be made to obtain the final construct, so long as the final construct possesses the desired characteristics, e.g., antigen binding. Thus, in certain embodiments, provided are antibody variants having one or more amino acid substitutions, sites of interest for substitution mutations include HVR and FR, e.g., amino acid substitutions can be introduced into an antibody of interest and products with desired activity are screened, e.g., retained/improved antigen binding, reduced immunogenicity, or improved ADCC or CDC.

EXAMPLES

The experimental methods used in the following examples are all conventional methods unless there are special requirements.

The materials, reagents, etc. used in the following examples can all be obtained from commercial sources unless otherwise specified.

Example 1 Preparation of Anti-Human TSLP Monoclonal Antibody QX008N

The Human thymic stromal lymphopoietin (hTSLP) was purchased from Novoprotein Scientific (Shanghai) Inc. and used to immunize New Zealand rabbits. B cell cloning technology was used to obtain antigen-binding specific antibody clones, and then monoclonal antibodies binding to human TSLP and having inhibitory activity against human TSLP were screened out. The cell supernatant was detected using Binding ELISA and Blocking ELISA to select target clones. The above immunization and screening processes were entrusted to commercialization companies for completion.

Seven clones were selected for recombinant expression and sequencing. It was determined that 8G2 had the best cell neutralizing activity. Therefore, the 8G2 clone was humanized. NCBI IgBlast was used to perform homology alignment of human IgG germline sequences (Germline), IGHV3-66*01 was selected as the heavy chain CDR transplantation template, and the CDR regions of the heavy chain (i.e., CDR-H1 (SEQ ID No: 1), CDR-H2 (SEQ ID No: 2) and CDR-H3 (SEQ ID No: 3)) of clone 8G2 were grafted into the framework region of IGHV3-66*01; IGKV1-12*01 was selected as the light chain CDR grafting template, and the CDR regions of the light chain (i.e., CDR-L1 (SEQ ID No: 4), CDR-L2 (SEQ ID No: 5), and CDR-L3 (SEQ ID No: 6)) of clone 8G2 were grafted into the framework region of IGKV1-12*01; reverse mutation was performed on the specific sites in the framework region to obtain the variable region of the monoclonal antibody QX008N of the present application. Finally, the sequence of the humanized heavy chain variable region was represented by SEQ ID NO: 7; and the amino acid sequence of the humanized light chain variable region was represented by SEQ ID NO: 8.

The genes of the heavy chain variable region (SEQ ID NO: 7) and the genes of the light chain variable region (SEQ ID NO: 8) were obtained by PCR amplification. The heavy chain expression plasmid pHZDCH was double-digested with HindIII and NheI; the light chain expression plasmid pHZDCK was double-digested with HindIII and BsiWI; the PCR amplified genes were inserted into the corresponding expression plasmids using Infusion recombinase to construct the heavy chain expression plasmid pHZDCH-8G2VH-Hu27 and light chain expression plasmid pHZDCK-8G2VK-Hu14.

The results of detecting the PCR-amplified variable region gene fragments and the double-digested plasmid by nucleic acid electrophoresis are shown in FIG. 1. According to the results in FIG. 1, the PCR amplification results of the antibody heavy chain variable region and light chain variable region and the results of double enzyme digestion of the heavy chain and light chain expression plasmids can be seen, wherein the plasmid sizes of the heavy chain and light chain are approximately 10000 bp, the heavy chain variable region is about 477 bp, and the light chain variable region is about 447 bp.

Figure 2:
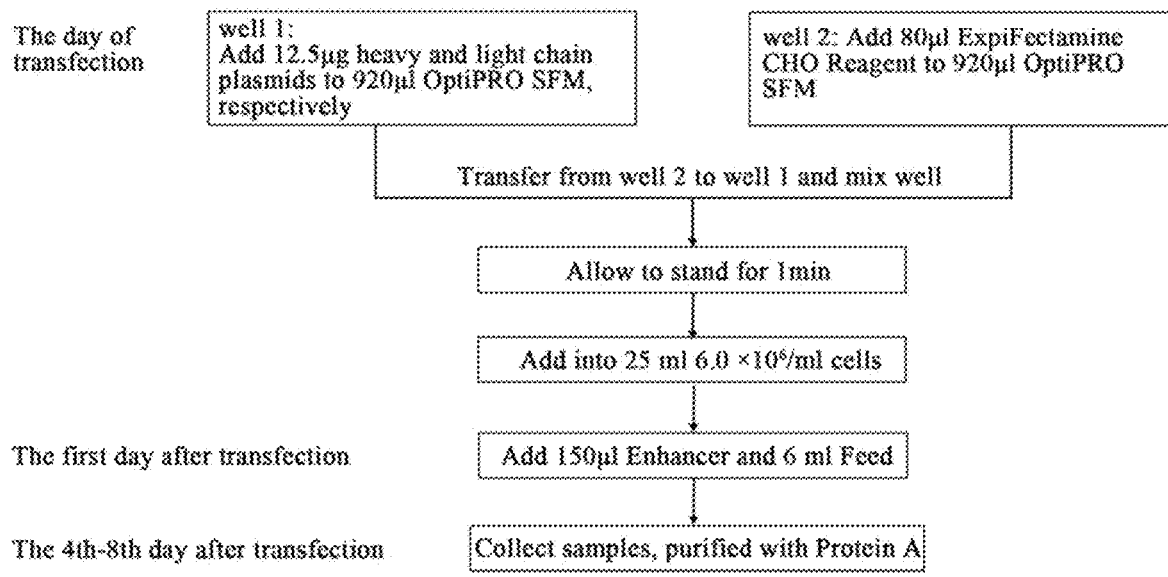
FIG. 2 is a flow chart of transient expression.

The heavy chain expression plasmid pHZDCH-8G2VH-Hu27 (the amino acid sequence of the expressed heavy chain is represented by SEQ ID NO: 10) and the light chain expression plasmid pHZDCK-8G2VK-Hu14 (the amino acid sequence of the expressed light chain is represented by SEQ ID NO: 11) with the correct sequence were co-transfected to ExpiCHO-S cells. The day before transfection, ExpiCHO-S cells were diluted to $3 \times 10^6$ cells/ml for passage before transfection. On the day of transfection, the cell were diluted to a cell density of $6 \times 10^6$ cells/ml, and 25 ml of cells were placed in a 125 ml shake flask, waiting for transfection. The process of transfection and expression is shown in FIG. 2.

Figure 3:
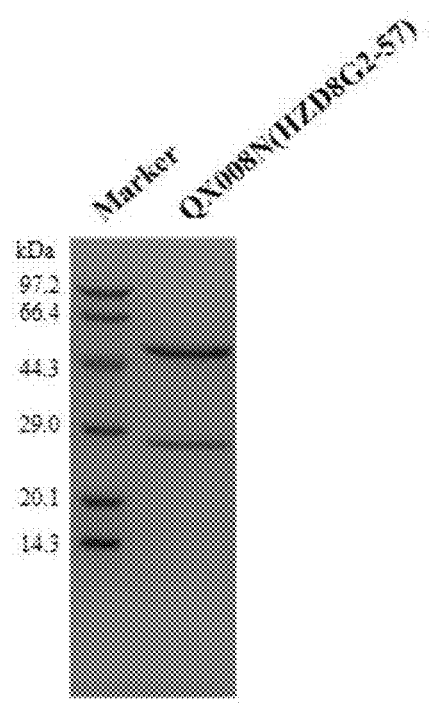
FIG. 3 shows the electrophoresis detection results of QX008N (HZD8G2-57).

On the $6^{th}$ day after transfection, the culture supernatant was harvested and subjected to one-step purification with Protein A. The purified antibody was detected by SDS-PAGE electrophoresis and named QX008N (HZD8G2-57). The results of detecting the antibody by protein electrophoresis are shown in FIG. 3. Protein electrophoresis was detected using denaturing reducing gel. The results in FIG. 3 shows two bands with sizes of approximately 50 kDa and 25 kDa respectively, which are consistent with the theoretical molecular weight of the heavy chain (49.3 kDa) and light chain (23.6 kDa).

Example 2 Determination of Equilibrium Dissociation Constant ($K_D$)

BIACORE™ T200 was used to detect the affinity of QX008N (HZD8G2-57) binding to human TSLP. All processes were performed at 25° C. A commercial Protein A chip was used to immobilize an appropriate amount of antibody through the capture method so that Rmax was around 50RU and the capture flow rate was 10 μl/min. The antigen was diluted by gradient, the flow rate of the instrument was switch to 30 μl/min, and the antigen flowed through the reference channel and the fixed antibody channel in order from low to high concentration, with the antigen flowing through the buffer as a negative control. After each binding and dissociation was completed, the chip was regenerated with glycine at pH 1.5. The 1:1 binding model in Kinetics option was selected for fitting using the analysis software that comes with the instrument, and the binding rate constant ka, the dissociation rate constant ka and the equilibrium dissociation constant $K_D$ value of the antibody were calculated.

In addition, the affinity of QX008N (HZD8G2-57) is compared with that of Tezepelumab, a monoclonal antibody against human TSLP that was currently in clinical phase III. The detection method for known antibodies was the same as that for QX008N. The results are shown in Table 1. Particularly, Tezepelumab was self-made by constructing an expression plasmid according to the A5 sequence provided by patent US20110274687A1, and transiently transfecting ExpiCHO-S cells.

TABLE 1

Affinity of anti-human TSLP monoclonal antibody binding to human TSLP

| Sample name | $k_a$ ($10^6$ M$^{-1}$S$^{-1}$) | $k_d$ ($10^{-5}$ S$^{-1}$) | $K_D$ ($10^{-11}$ M) |
|---|---|---|---|
| QX008N | 1.74 | 2.99 | 1.75 |
| Tezepelumab | 2.70 | 6.46 | 2.38 |

The data in the table is the average value calculated after each sample is tested for three times.

Example 3 Activities of QX008N and Tezepelumab Neutralizing STAT5 Phosphorylation in SW756-STAT5-Luciferase Reporter Gene Cells Induced by Human TSLP The SW756-STAT5-Luciferase reporter gene cell line was used to measure the activity of QX008N antagonizing phosphorylation of the intracellular signaling molecule STAT5 mediated by human TSLP through TSLPR-IL-7R: cells in the culture medium were added to 96 wells with $4 \times 10^4$ cells per well, and cultured overnight at 37° C. and 5% $CO_2$; the mixture of pre-incubated antibody and human TSLP was added to the cells, wherein the final concentration range of QX008N was 0 to 50 ng/ml, the final concentration range of Tezepelumab was 0 to 400 ng/ml, and the final concentration of TSLP was 0.5 ng/ml, then incubated at 37° C. and 5% $CO_2$ for 24 hours; the cell culture supernatant was discarded, 120 μl of ONE-Glo™-Luciferase Reagent for detection was added to each well, reacting for 30 min, taking 100 μl of sample from each well to a white 96-well plate to detect the fluorescence signal value and draw a dose-effect curve, thereby analyzing the antagonistic activity of the antibody. The dose-effect curve is shown in FIG. 4.

Figure 4:
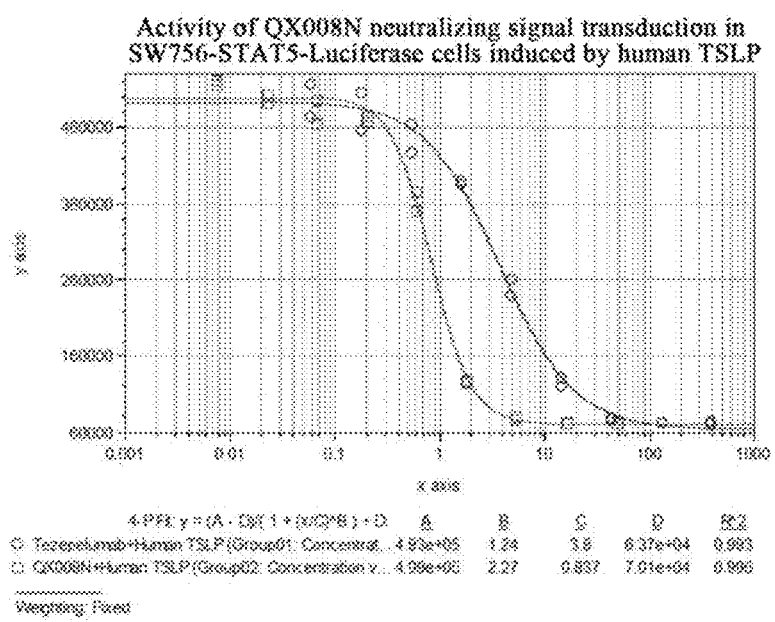
FIG. 4 shows the activities of QX008N and Tezepelumab neutralizing STAT5 phosphorylation in SW756-STAT5 Luciferase cells induced by human TSLP.

The results shown in FIG. 4 shows that QX008N can inhibit STAT5 phosphorylation in SW756-STAT5-Luciferase reporter gene cells induced by human TSLP. The $IC_{50}$ of QX008N inhibiting the activity of STAT5 phosphorylation in SW756-STAT5-Luciferase reporter gene cells induced by human TSLP is 0.837 ng/ml, while the $IC_{50}$ of Tezepelumab inhibiting the activity of STAT5 phosphorylation in SW756-STAT5-Luciferase reporter gene cells induced by human TSLP is 3.8 ng/ml.

Example 4 Activities of QX008N and Tezepelumab Neutralizing STAT5 Phosphorylation in SW756-STAT5-Luciferase Reporter Gene Cells Induced by Natural TSLP The SW756-STAT5-Luciferase reporter gene cell line was used to measure the activity of QX008N antagonizing phosphorylation of the intracellular signaling molecule STAT5 mediated by natural TSLP through TSLPR-IL-7R: cells in the culture medium were added to 96 wells with $4 \times 10^4$ cells per well and then cultured overnight at 37° C. and 5% $CO_2$; the mixture of pre-incubated antibody and natural TSLP was added to the cells, wherein the final concentration range of QX008N was 0 to 50 ng/ml, the final concentration range of Tezepelumab was 0 to 400 ng/ml, and the final concentration of natural TSLP was the concentration after diluting the stock solution 62.5 times, then incubated at 37° C. and 5% $CO_2$ for 24 hours; the cell culture supernatant was discarded, 120 μl of ONE-Glo™-Luciferase Reagent for detection was added to each well, reacting for 30 min, taking 100 μl of sample from each well to a white 96-well plate to detect the fluorescence signal value and draw a dose-effect curve, thereby analyzing the antagonistic activity of the antibody. The dose-effect curve is shown in FIG. 5.

Figure 5:
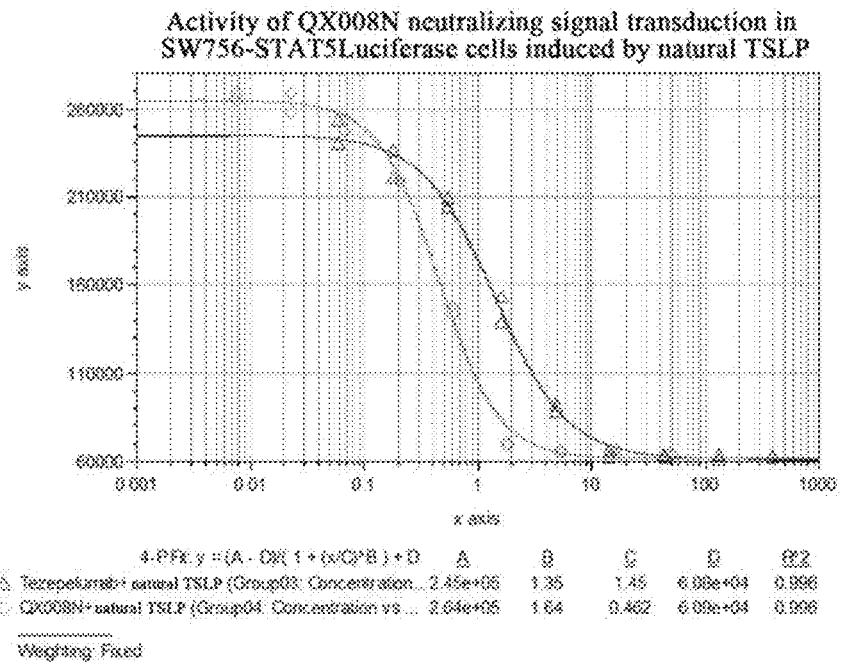
FIG. 5 shows the activities of QX008N and Tezepelumab neutralizing STAT5 phosphorylation in SW756-STAT5-Luciferase reporter gene cells induced by natural TSLP.

The results shown in FIG. 5 shows that QX008N can inhibit STAT5 phosphorylation in SW756-STAT5-Luciferase reporter gene cells induced by natural TSLP. The $IC_{50}$ of QX008N inhibiting the activity of STAT5 phosphorylation in SW756-STAT5-Luciferase reporter gene cells induced by natural TSLP is 0.462 ng/ml, while the $IC_{50}$ of Tezepelumab inhibiting the activity of STAT5 phosphorylation in SW756-STAT5-Luciferase reporter gene cells induced by natural TSLP is 1.45 ng/ml.

Example 5 Activities of QX008N and Tezepelumab Neutralizing STAT5 Phosphorylation in SW756-STAT5-Luciferase Reporter Gene Cells Induced by Cynomolgus Monkey TSLP The SW756-STAT5-Luciferase reporter gene cell line was used to measure the activity of QX008N antagonizing phosphorylation of the intracellular signaling molecule STAT5 mediated by Cynomolgus monkey TSLP through TSLPR-IL-7R: cells in the culture medium were added to 96 wells with $4 \times 10^4$ cells per well and then cultured overnight at 37° C. and 5% $CO_2$; the mixture of pre-incubated antibody and Cynomolgus monkey TSLP was added to the cells, wherein the final concentration range of QX008N was 0 to 50 ng/ml, the final concentration range of Tezepelumab was 0 to 400 ng/ml, and the final concentration of Cynomolgus monkey TSLP was 0.5 ng/ml, then incubated at 37° C. and 5% $CO_2$ for 24 hours; the cell culture supernatant was discarded, 120 µl of ONE-Glo™-Luciferase Reagent for detection was added to each well, reacting for 30 min, taking 100 µl of sample from each well to a white 96-well plate to detect the fluorescence signal value and draw a dose-effect curve, thereby analyzing the antagonistic activity of the antibody. The dose-effect curve is shown in FIG. 6.

Figure 6:
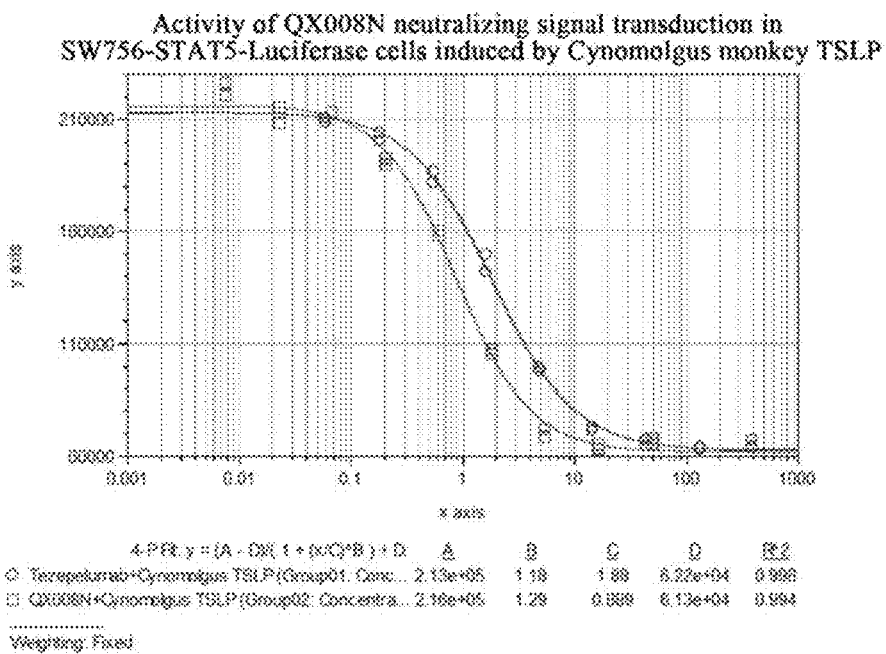
FIG. 6 shows the activities of QX008N and Tezepelumab neutralizing STAT5 phosphorylation in SW756-STAT5-Luciferase reporter gene cells induced by cynomolgus monkey TSLP.

The results shown in FIG. 6 shows that QX008N can inhibit the activity of STAT5 phosphorylation in SW756-STAT5-Luciferase reporter gene cells induced by Cynomolgus monkey TSLP. The $IC_{50}$ of QX008N inhibiting the activity of STAT5 phosphorylation in SW756-STAT5-Luciferase reporter gene cells induced by Cynomolgus monkey TSLP is 0.889 ng/ml, while the $IC_{50}$ of Tezepelumab inhibiting the activity of STAT5 phosphorylation in SW756-STAT5-Luciferase reporter gene cells induced by Cynomolgus monkey TSLP is 1.88 ng/ml.

Example 6 Activities of QX008N and Tezepelumab Neutralizing the Release of TARC (CCL17) from Human Whole Blood Induced by Human TSLP The human whole blood was used to measure the activity of QX008N antagonizing the release of TARC (CCL17) mediated by human TSLP through TSLPR-IL-7R: the human whole blood was added to a 96-well plate with 100 µl per well and temporarily stored at 37° C. and 5% $CO_2$; the mixture of pre-incubated antibody and human TSLP was added to the human whole blood, wherein the final concentration range of antibody was 0 to 50 ng/ml, and the final concentration of human TSLP was 0.5 ng/ml, and IL-33 with a final concentration of 0.5 ng/ml was added, culturing at 37° C. and 5% $CO_2$ for 48 hours; the cell culture supernatant was collected and sandwich ELISA was used to detect the expression of TARC (CCL17) in the supernatant, and a dose-effect curve was drawn to analyze the antagonistic activity of the antibody. The dose-effect curve is shown in FIG. 7.

Figure 7:
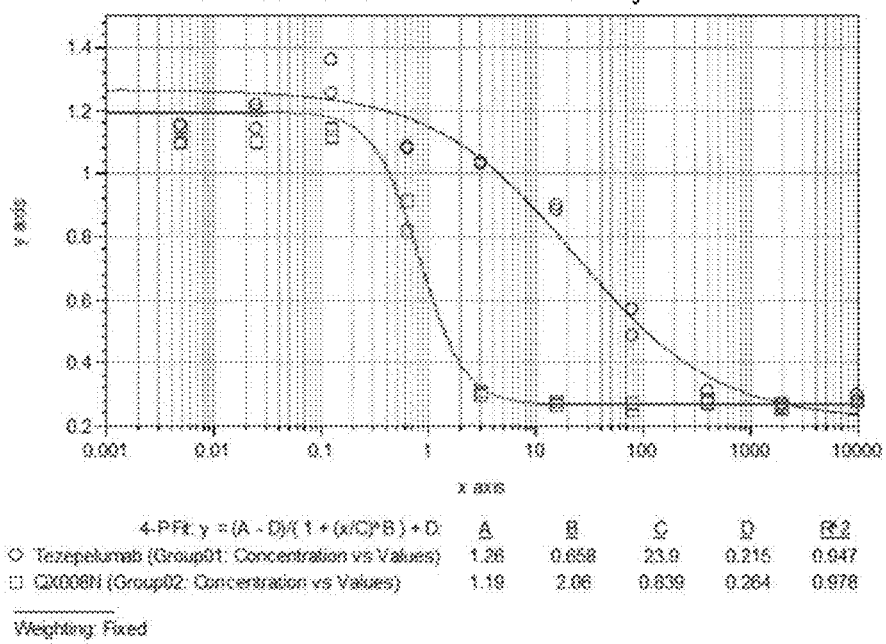
FIG. 7 shows the activities of QX008N and Tezepelumab neutralizing the release of TARC (CCL17) from human whole blood induced by human TSLP.

The results shown in FIG. 7 shows that QX008N can inhibit the release of TARC (CCL17) from human whole blood induced by human TSLP. The $IC_{50}$ of QX008N inhibiting the activity of releasing TARC (CCL17) from human whole blood induced by human TSLP is 0.839 ng/ml, while the $IC_{50}$ of Tezepelumab inhibiting the activity of releasing TARC (CCL17) from human whole blood induced by human TSLP is 23.9 ng/ml.

Example 7 Activities of QX008N and Tezepelumab Neutralizing the Release of TARC (CCL17) from Human PBMCs Induced by Human TSLP The human PBMC cells were used to measure the activity of QX008N antagonizing the release of TARC (CCL17) mediated by human TSLP through TSLPR-IL-7R: PBMCs were separated by density gradient centrifugation. PBMCs were added to a 96-well plate with 300000 cells per well and temporarily stored at 37° C. and 5% $CO_2$; the mixture of pre-incubated antibodies and human TSLP was added to PBMCs, wherein the final concentration range of antibody 0 to 10 µg/ml, the final concentration of human TSLP was 0.5 ng/ml, and IL-33 with a final concentration of 0.5 ng/ml was added, culturing at 37° C. and 5% $CO_2$ for 48 hours; the cell culture supernatant was collected and sandwich ELISA was used to detect the expression of TARC (CCL17) in the supernatant, and a dose-effect curve was drawn to analyze the antagonistic activity of the antibody. The dose-effect curve is shown in FIG. 8.

Figure 8:
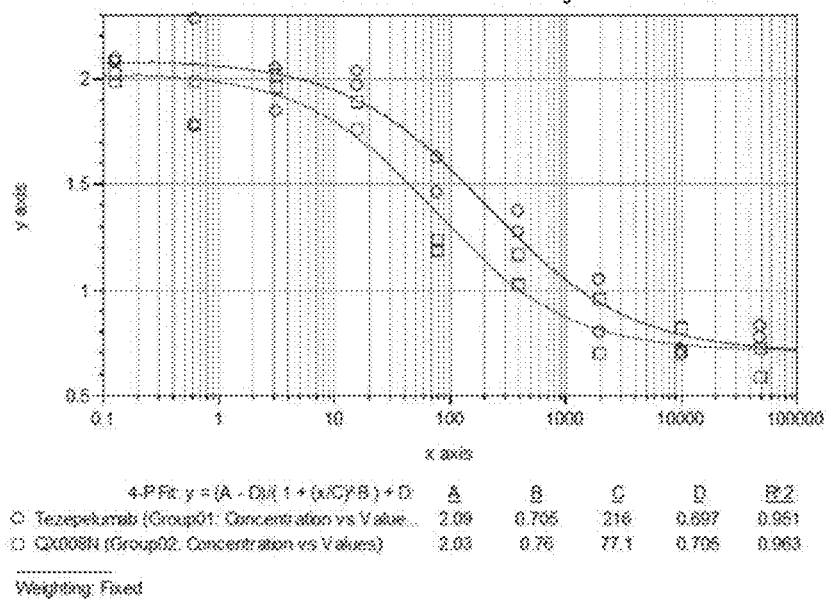
FIG. 8 shows the activities of QX008N and Tezepelumab neutralizing the release of TARC (CCL17) from human PBMC cells induced by human TSLP.

The results shown in FIG. 8 shows that QX008N can inhibit the release of TARC (CCL17) from PBMCs induced by human TSLP. The $IC_{50}$ of QX008N inhibiting the activity of releasing TARC (CCL17) from PBMCs induced by human TSLP is 77.1 ng/ml, while the $IC_{50}$ of Tezepelumab inhibiting the activity of releasing TARC (CCL17) from PBMCs induced by human TSLP is 216 ng/ml.

Although the embodiments of the present application have been described above, the present application is not limited to the above-mentioned specific embodiments and application fields. The above-mentioned specific embodiments are only illustrative and instructive, rather than restrictive. Those of ordinary skill in the art can also make many forms under the inspiration of this description and without departing from the scope of protection of the claims of the present application, and these are all included in the protection of the present application.

The invention claimed is:

1. An anti-human thymic stromal lymphopoietin (TSLP) monoclonal antibody, comprising three heavy chain complementarity determining regions (CDR-H1, CDR-H2 and CDR-H3) and three light chain complementarity determining regions (CDR-L1, CDR-L2 and CDR-L3), wherein:
the amino acid sequence of CDR-H1 is represented by SEQ ID NO: 1;
the amino acid sequence of CDR-H2 is represented by SEQ ID NO: 2;
the amino acid sequence of CDR-H3 is represented by SEQ ID NO: 3;
the amino acid sequence of CDR-L1 is represented by SEQ ID NO: 4;
the amino acid sequence of CDR-L2 is represented by SEQ ID NO: 5; and
the amino acid sequence of CDR-L3 is represented by SEQ ID NO: 6.

2. The monoclonal antibody according to claim 1, which comprises a heavy chain variable region and a light chain variable region, wherein
the amino acid sequence of the heavy chain variable region is represented by SEQ ID NO: 7; and
the amino acid sequence of the light chain variable region is represented by SEQ ID NO: 8.

3. A pharmaceutical composition, which comprises the monoclonal antibody according to claim 1 and a pharmaceutically acceptable carrier.

4. The pharmaceutical composition according to claim 3, which is used for treating a disease related to TSLP-mediated signal transduction.

5. The pharmaceutical composition according to claim 4, wherein the disease related to TSLP-mediated signal transduction is selected from the group consisting of: allergic asthma, allergic dermatitis, allergic rhinitis, allergic conjunctivitis, atopic dermatitis, and fibrosis.

6. A method of treating a disease related to TSLP-mediated signal transduction, comprising
administering the monoclonal antibody of claim 1, or a pharmaceutical composition comprising the monoclonal antibody of claim 1 and a pharmaceutically acceptable carrier, to a subject in need thereof,
wherein the disease related to TSLP-mediated signal transduction-related is selected from the group consisting of: allergic asthma, allergic dermatitis, allergic rhinitis, allergic conjunctivitis, atopic dermatitis, and fibrosis.

* * * * *

SEQUENCE LISTING

```
Sequence total quantity: 11
SEQ ID NO: 1            moltype = AA  length = 5
FEATURE                 Location/Qualifiers
REGION                  1..5
                        note = Description of Artificial Sequence: artificially
                        synthesized sequence
source                  1..5
                        mol_type = protein
                        organism = synthetic construct
SEQUENCE: 1
SYYMS                                                                    5

SEQ ID NO: 2            moltype = AA  length = 16
FEATURE                 Location/Qualifiers
REGION                  1..16
                        note = Description of Artificial Sequence: artificially
                        synthesized sequence
source                  1..16
                        mol_type = protein
                        organism = synthetic construct
SEQUENCE: 2
FISYGGSAYH ATWAQG                                                       16
```

```
SEQ ID NO: 3            moltype = AA   length = 13
FEATURE                 Location/Qualifiers
REGION                  1..13
                        note = Description of Artificial Sequence: artificially
                         synthesized sequence
source                  1..13
                        mol_type = protein
                        organism = synthetic construct
SEQUENCE: 3
EFRSMTYGAE WGI                                                              13

SEQ ID NO: 4            moltype = AA   length = 11
FEATURE                 Location/Qualifiers
REGION                  1..11
                        note = Description of Artificial Sequence: artificially
                         synthesized sequence
source                  1..11
                        mol_type = protein
                        organism = synthetic construct
SEQUENCE: 4
QASESIYDTL A                                                                11

SEQ ID NO: 5            moltype = AA   length = 7
FEATURE                 Location/Qualifiers
REGION                  1..7
                        note = Description of Artificial Sequence: artificially
                         synthesized sequence
source                  1..7
                        mol_type = protein
                        organism = synthetic construct
SEQUENCE: 5
SASSLAS                                                                     7

SEQ ID NO: 6            moltype = AA   length = 13
FEATURE                 Location/Qualifiers
REGION                  1..13
                        note = Description of Artificial Sequence: artificially
                         synthesized sequence
source                  1..13
                        mol_type = protein
                        organism = synthetic construct
SEQUENCE: 6
QQGYTMPDVD KNP                                                              13

SEQ ID NO: 7            moltype = AA   length = 121
FEATURE                 Location/Qualifiers
REGION                  1..121
                        note = Description of Artificial Sequence: artificially
                         synthesized sequence
source                  1..121
                        mol_type = protein
                        organism = synthetic construct
SEQUENCE: 7
EVQLVESGGG LVQPGGSLRL SCAASGFSLS SYYMSWVRQA PGKGLEWVGF ISYGGSAYHA           60
TWAQGRFTIS KDNSKNTLYL QMNSLRAEDT AVYYCAREFR SMTYGAEWGI WGQGTLVTVS          120
S                                                                         121

SEQ ID NO: 8            moltype = AA   length = 111
FEATURE                 Location/Qualifiers
REGION                  1..111
                        note = Description of Artificial Sequence: artificially
                         synthesized sequence
source                  1..111
                        mol_type = protein
                        organism = synthetic construct
SEQUENCE: 8
AYQMTQSPSS VSASVGDRVT ITCQASESIY DTLAWYQQKP GKAPKLLIYS ASSLASGVPS           60
RFSGSGSGTD FTLTISSLQP EDFATYYCQQ GYTMPDVDKN PFGGGTKVEI K                   111

SEQ ID NO: 9            moltype = AA   length = 159
FEATURE                 Location/Qualifiers
REGION                  1..159
                        note = Description of Artificial Sequence: artificially
                         synthesized sequence
source                  1..159
                        mol_type = protein
                        organism = synthetic construct
```

```
SEQUENCE: 9
MFPFALLYVL SVSFRKIFIL QLVGLVLTYD FTNCDFEKIK AAYLSTISKD LITYMSGTKS    60
TEFNNTVSCS NRPHCLTEIQ SLTFNPTAGC ASLAKEMFAM KTKAALAIWC PGYSETQINA   120
TQAMKKRRKR KVTTNKCLEQ VSQLQGLWRR FNRPLLKQQ                          159

SEQ ID NO: 10           moltype = AA  length = 451
FEATURE                 Location/Qualifiers
REGION                  1..451
                        note = Description of Artificial Sequence: artificially
                          synthesized sequence
source                  1..451
                        mol_type = protein
                        organism = synthetic construct
SEQUENCE: 10
EVQLVESGGG LVQPGGSLRL SCAASGFSLS SYYMSWVRQA PGKGLEWVGF ISYGGSAYHA    60
TWAQGRFTIS KDNSKNTLYL QMNSLRAEDT AVYYCAREFR SMTYGAEWGI WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 11           moltype = AA  length = 218
FEATURE                 Location/Qualifiers
REGION                  1..218
                        note = Description of Artificial Sequence: artificially
                          synthesized sequence
source                  1..218
                        mol_type = protein
                        organism = synthetic construct
SEQUENCE: 11
AYQMTQSPSS VSASVGDRVT ITCQASESIY DTLAWYQQKP GKAPKLLIYS ASSLASGVPS    60
RFSGSGSGTD FTLTISSLQP EDFATYYCQQ GYTMPDVDKN PFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218
```